Figure 1:
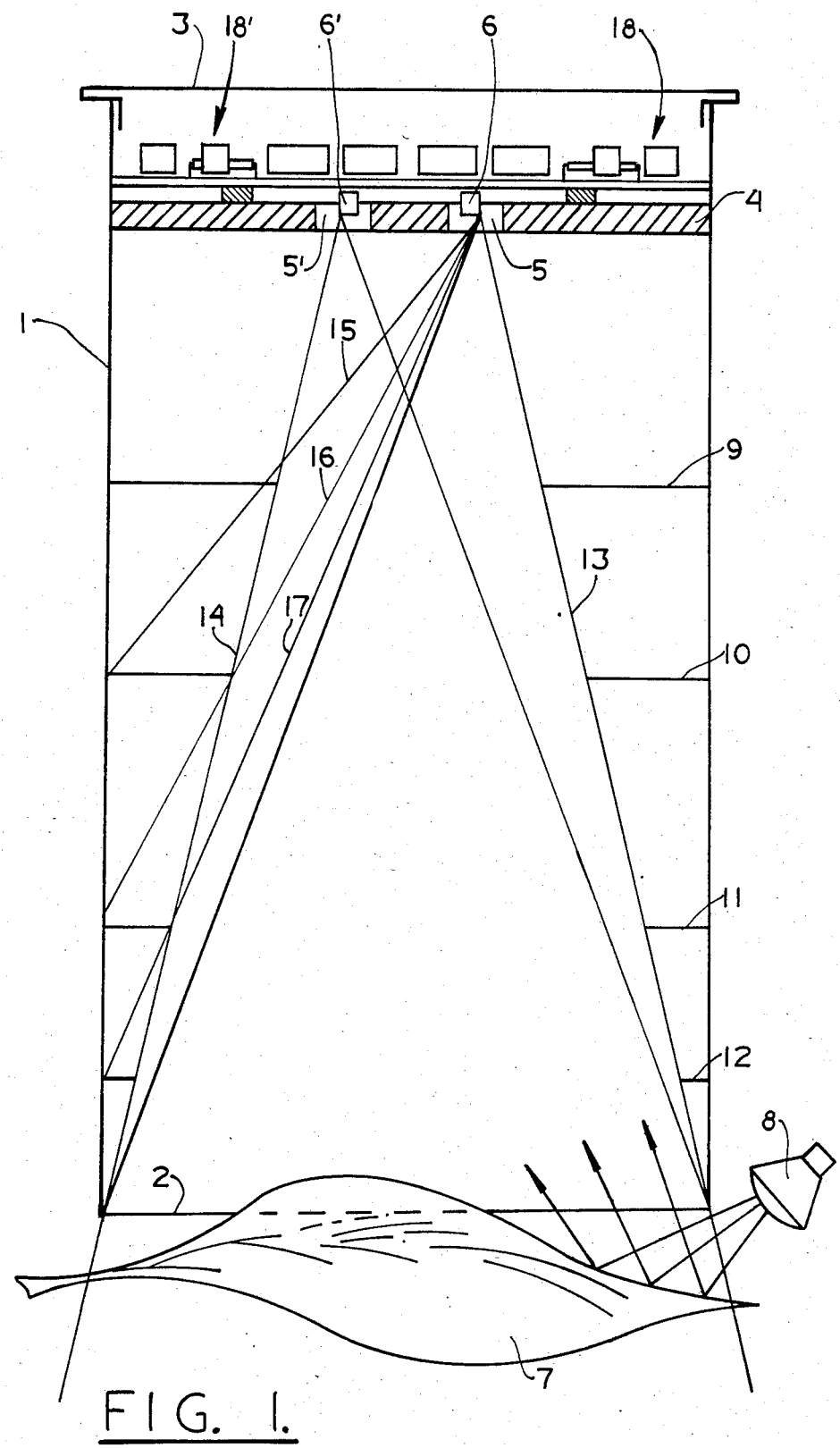

United States Patent [19]

Hristozov et al.

[11] Patent Number: 4,603,251

[45] Date of Patent: Jul. 29, 1986

[54] DEVICE FOR DETERMINING THE REFLECTIVE CHARACTERISTICS OF ARTICLES

[75] Inventors: Vladislav N. Hristozov; Zdravko B. Marchev, both of Sofia; Hristo M. Ribarov; Spas N. Markov, both of Plovdiv, all of Bulgaria

[73] Assignee: Institute po Technicheska Kibernetika i Robotika, Sofia, Bulgaria

[21] Appl. No.: 544,576

[22] Filed: Oct. 24, 1983

[30] Foreign Application Priority Data

Oct. 22, 1982 [BG] Bulgaria .................................. 58373

[51] Int. Cl.⁴ ............................. G01J 3/50; H01J 5/16
[52] U.S. Cl. ................................. 250/226; 250/237 R; 350/276 SL
[58] Field of Search ................... 250/237 R, 226, 571, 250/572; 209/576, 577, 580, 581; 350/449, 319, 276 R, 276 SL

[56] References Cited

U.S. PATENT DOCUMENTS

| 2,670,656 | 3/1954 | Braymer | 350/276 SL |
| 3,016,798 | 1/1962 | Lawrence | 350/276 SL |
| 4,150,287 | 4/1979 | Perkins | 250/227 |
| 4,217,026 | 8/1980 | Radovich | 350/276 SL |

Primary Examiner—David C. Nelms
Assistant Examiner—Lark W. Madoo

[57] ABSTRACT

Device for determining the reflective properties of objects in discrete spectral zones. The device has a housing in which there is disposed a diaphragm perpendicularly to the optical axis of the device and photosensors sensitive to light in a narrow spectral range that are connected with electronic amplifiers. The opening of the diaphragm coincides with the basic aperture of vision. Between the diaphragm and the object there are disposed supplementary diaphragms with openings coinciding with the basic aperture of vision. Each supplementary diaphragm lies in a plane determined by the intersection point of the parasitic aperture of vision of the diaphragm preceding it on the side of the photosensors and the housing. The device may be use to advantage in color discriminating systems, for example, the sorting of tobacco leaves according to their color.

1 Claim, 1 Drawing Figure

DEVICE FOR DETERMINING THE REFLECTIVE CHARACTERISTICS OF ARTICLES

This invention relates to a device for determining the reflective properties of articles in discrete spectral zones, and is used in systems for color discrimination, for example, the sorting of tobacco in accordance with its color.

U.S. Pat. No. 4,150,287 to Perkins discloses a device for determining the reflective capacity of objects in discrete spectral zones. Such known device comprises a housing and a lens focusing the image of the object on a diaphragm disposed in the housing perpendicularly to its optical axis. The opening of the diaphragm coincides with the essential vision aperture. Above the diaphragm there is disposed an optical lens focusing the image of the object on a bundle of optical fibers, the first end of the bundle being at or near the image plane on the side thereof opposite the lens, the bundle of fibers forwarding the light to a plurality of light filter means from which the light travels to a plurality of photo detector means each arranged to receive light passed by a respective filter means. The photosensors are sensitive to light in a narrow spectral range, and are connected to electronic amplifiers.

The disadvantages of such known device is the need of a lens, light conducting devices such as optical fibers, and light filter means, the latter substantially reducing the light flux forwarded to the photosensors. Distortions are produced, owing to geometric and chromatic aberrations that result in a dependence of the signals received by the photosensors not only upon the reflecting capacity of the object in the spectral zones defined by the color filters, but also from its location in the boundary zones of the field of vision of the device. These distortions cause errors in the measurement of the reflecting capacity of the object being tested.

The present invention has among its objects the provision of a novel device for determining the reflecting capacity of objects in narrow spectral zones, such device having an increased accuracy and being of simplified construction.

The above aim is achieved by a device for determining the reflecting capacity of objects comprising a housing in which there is disposed a diaphragm perpendicularly to the optical axis, and photosensors sensitive to light in a narrow spectral range that are connected to electronic amplifiers, the opening of the diaphragm coinciding with the basic vision aperture of the device. Between the diaphragm and the object there are placed supplementary diaphragms with openings coinciding with the basic vision aperture, every supplementary diaphragm lying in a plane determined by the intersection point of the parasitic aperture of vision of the diaphragm which precedes it on the side of the photosensors and the housing.

An advantage of the device of the invention is that the light flux reflected by the object being tested directly reaches the photosensors, and hence insures a high level of the signals produced by them and a reduced dependence of the signals upon the location of the object in the field of vision of the device, such device being of a simplified construction.

Reference will be made, by way of example, to the accompanying drawing, wherein:

The single FIGURE of the drawing is a schematic view in longitudinal axial section of a preferred embodiment of the device of the invention.

Turning now to the drawing, the embodiment of the device of the invention there shown comprises an elongated housing 1 having an open end 2 and a closed end 3, both of such ends being disposed transverse to the longitudinal axis of the housing. A transverse partition 4 is disposed in the housing near but spaced from the closed end 3 thereof. The partition 4 has a plurality (two shown) of openings 5 and 5' therethrough spaced transversely of the housing, in each of the openings 5, 5' there being disposed a respective photosensor 6, 6'. An object to be tested, such as a tobacco leaf 7, is disposed adjacent the opening 2 in the housing, and is obliquely illuminated by a light source 8. Light from source 8 falls upon the upper surface of the leaf 7 and is reflected therefrom upwardly in the housing 1 toward the partition 4 therein.

A first diaphragm 9, positioned closest to the partition 4 and disposed transversely of the longitudinal axis of the housing 1 ensures a shadowing of the part of the housing disposed between the diaphragm 9 and the plane of the photosensors 5, 5'. A plurality of supplementary transverse diaphragms 10, 11 and 12 are provided, such supplementary diaphragms being disposed transversely of the longitudinal axis of housing 1 and spaced therealong, as shown. The supplementary diaphragms lie in planes determined by the intersection point of the parasitic aperture of vision defined by the primary diaphragm 9 and the outer edges of the opening 2 at the lower end of the housing, as shown. Thus the inner edges of all of the diaphragms 9, 10, 11, and 12 lie upon lines 13 and 14 which extend, respectively, from the lower right hand corner of the opening 2 to the right hand corner of the photosensor 6, and from the left hand lower corner of the opening 2 of the housing to the left hand corner of the photosensor 6'. As is illustrated by the lines 15, 16 and 17, the supplementary diaphragms 10, 11 and 12 intercept parasitic reflections from the partition 4 and the photosensors 6, 6'. The photosensors 6, 6' are connected respectively to electronic amplifiers 18, 18'.

The above-described device operates as follows:

The object 7 being tested is illuminated by a source 8 of polychromatic light. The light reflected from the part of object 7 illuminated by light source 8 is perceived by the photosensors 6, 6'. The signals forwarded to amplifiers 18, 18' are in a direct proportion to the reflective capacity of the object 7 in zones determined by the spectral ranges of sensitivity of the photosensors 6, 6'. The light reflected by objects located outside of the essential vision aperture of the device falls on the supplemental diaphragms 10, 11 and 12 and the internal parts of the housing 1, and is absorbed by light absorbing layers of covering material (not shown) on such diaphragms and the internal surfaces of the housing.

Although the invention is described and illustrated with reference to single embodiment thereof, it is to be expressly understood that it is in no way limited to the disclosure of such preferred embodiments but is capable of numerous modifications within the scope of the appended claims.

We claim:

1. A device for determining the reflective capacity of objects, comprising an elongated housing having one open end and one closed end, photosensors sensitive to light in a narrow spectral range being disposed adjacent to the closed end of the housing, electronic amplifiers connected to the output of respective photosensors, a plurality of diaphragms extending transversely of the longitudinal axis of the housing and spaced therealong, said plurality of diaphragms being composed of a first diaphragm which is disposed closest to the photosensors, said first diaphragm having an opening therethrough coinciding with the essential aperture of vision of the device, the others of said plurality of a diaphragms being supplementary diaphragms with openings therethrough coinciding with the essential aperture of vision, the supplementary diaphragms being disposed in spaced relationship between the first diaphragm and the open end of the housing, every supplementary diaphragm lying in the plane determined by the intersection point of the parasitic aperture of vision of the diaphragm preceding it on the side of the photosensors and the edge of the housing at the open end thereof.

* * * * *